(12) United States Patent
Rha et al.

(10) Patent No.: US 10,111,922 B2
(45) Date of Patent: Oct. 30, 2018

(54) PREPARATION METHOD OF TEA WATER, AND TEA WATER OBTAINED THEREBY

(71) Applicant: AMOREPACIFIC CORPORATION, Seoul (KR)

(72) Inventors: Chan S. Rha, Gyeonggi-do (KR); Yu J. Oh, Gyeonggi-do (KR); Jin O. Chung, Gyeonggi-do (KR); Se J. Yoo, Gyeonggi-do (KR); Sang J. Lee, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 216 days.

(21) Appl. No.: 14/499,506

(22) Filed: Sep. 29, 2014

(65) Prior Publication Data

US 2015/0044307 A1      Feb. 12, 2015

Related U.S. Application Data

(62) Division of application No. 13/512,538, filed as application No. PCT/KR2010/008517 on Nov. 30, 2010, now abandoned.

(30) Foreign Application Priority Data

Nov. 30, 2009   (KR) .................. 10-2009-0116703

(51) Int. Cl.
| | | |
|---|---|---|
| *A61K 36/82* | (2006.01) | |
| *A23F 3/18* | (2006.01) | |
| *A23F 3/20* | (2006.01) | |
| *A61K 8/97* | (2017.01) | |
| *A61Q 19/00* | (2006.01) | |

(52) U.S. Cl.
CPC ............ *A61K 36/82* (2013.01); *A23F 3/18* (2013.01); *A23F 3/20* (2013.01); *A61K 8/97* (2013.01); *A61Q 19/00* (2013.01); *A23V 2002/00* (2013.01)

(58) Field of Classification Search
CPC ................................................... A61K 36/82
See application file for complete search history.

(56) References Cited

U.S. PATENT DOCUMENTS

| | | | | |
|---|---|---|---|---|
| 4,639,375 A | * | 1/1987 | Tsai .......................... | A23F 3/10 426/49 |
| 5,198,259 A | * | 3/1993 | Hoogstad .................. | A23F 3/22 426/388 |
| 2006/0003033 A1 | | 1/2006 | McClellan et al. | |

FOREIGN PATENT DOCUMENTS

| | | | |
|---|---|---|---|
| CH | EP 0547370 A2 * | 6/1993 | ........... A23L 3/3472 |
| CN | 1075849 A | 9/1993 | |
| CN | 101366425 A | 2/2009 | |
| EP | 1 839 492 A1 | 10/2007 | |
| JP | 06116258 A * | 4/1994 | |
| JP | 08-081325 A | 3/1996 | |
| JP | 08-298930 A | 11/1996 | |
| JP | 11018678 A * | 1/1999 | |
| JP | 2003-252720 A | 9/2003 | |
| JP | 2005-287312 A | 10/2005 | |
| JP | 2006061125 A | 3/2006 | |
| JP | 2006241007 A * | 9/2006 | |
| JP | 2007-082526 A | 4/2007 | |
| JP | 2007-302577 A | 11/2007 | |
| JP | 2008-520593 A | 6/2008 | |
| JP | 2009-153487 A | 7/2009 | |
| JP | 2009-249318 A | 10/2009 | |
| KR | 2001-0035409 A | 5/2001 | |
| KR | 2001-0035410 A | 5/2001 | |
| KR | 10-2002-0040099 A | 5/2002 | |
| KR | 10-2009-0056612 A | 6/2009 | |
| WO | WO 2006/053458 A1 | 5/2006 | |
| WO | WO 2009/059928 A1 | 5/2009 | |

OTHER PUBLICATIONS

Shigeru Sekine (Representative) New Cosmetic Handbook, No. 219, vol. 2, pp. 491-492, Oct. 30, 2006.
J. J. Hostynek et al., "A Dermatological View, Allergic Contact Dermatitis to Linalool," Cosmetics and Toiletries, vol. 122, No. 11, pp. 30, 32-34, 36, Nov. 2007.
P. Schreier et al., "Aroma of Black Tea. Preparation of a Tea Concentrate by Reverse Osmosis and its Analytical Characterization." Zeitschrift Fur Lebensmittel Untersuchung und-Forschung, vol. 179, No. 2, pp. 113-118, Aug. 1984.
"How to use loose tea to make tea". Internet Archive Date: Mar. 15, 2009. [Retrieved from the internet on: Jul. 29, 2013]. Retrieved from: <URL: http://web.archive.org/web/20090315094402/http://www.wikihow.com/Use-Loose-Tea-to-Make-Tea>.

* cited by examiner

*Primary Examiner* — Amy L Clark
(74) *Attorney, Agent, or Firm* — Blank Rome LLP

(57) ABSTRACT

The present invention provides a preparation method of tea water comprising the following steps of: inactivating enzymes of raw tea leaves and juicing the tea leaves to obtain a tea juice; and removing ions of the tea juice obtained from the previous step to obtain tea water. In addition, the present invention provides tea water obtained by removing ions from a tea juice of raw tea leaves of which enzymes are inactivated. Skin-stimulating components are reduced in the tea water.

5 Claims, 3 Drawing Sheets

【Figure 1】
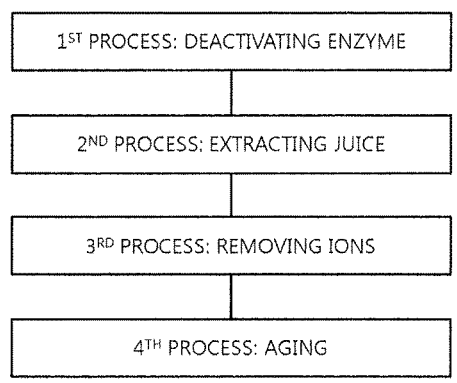
【Figure 2】
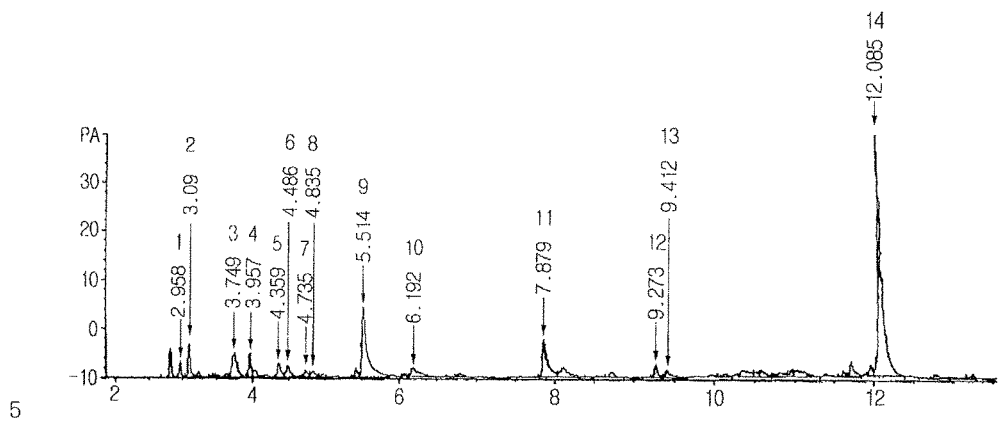
【Figure 3】
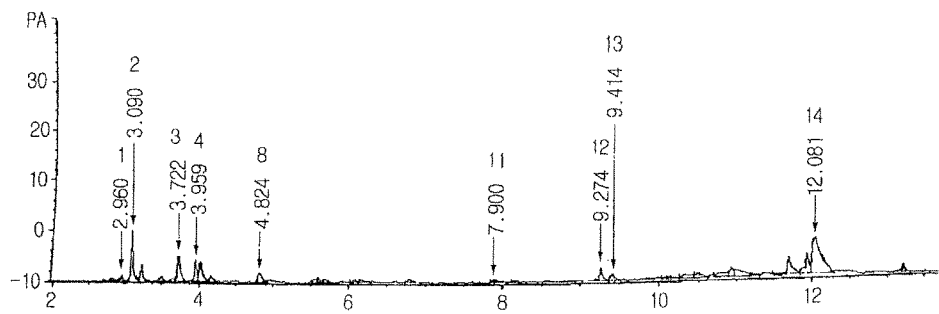

[Figure 4]
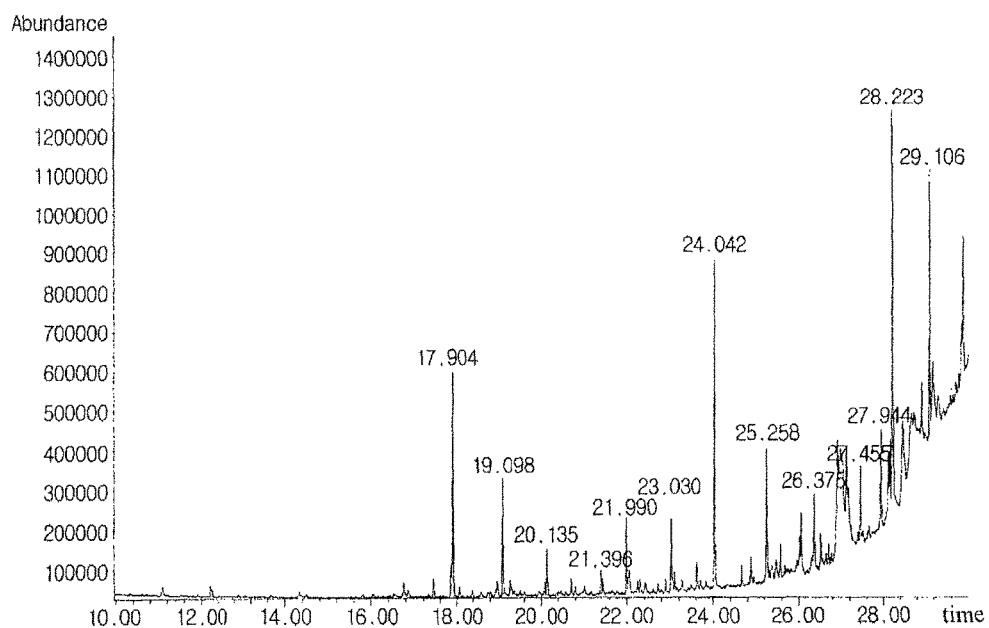
[Figure 5]
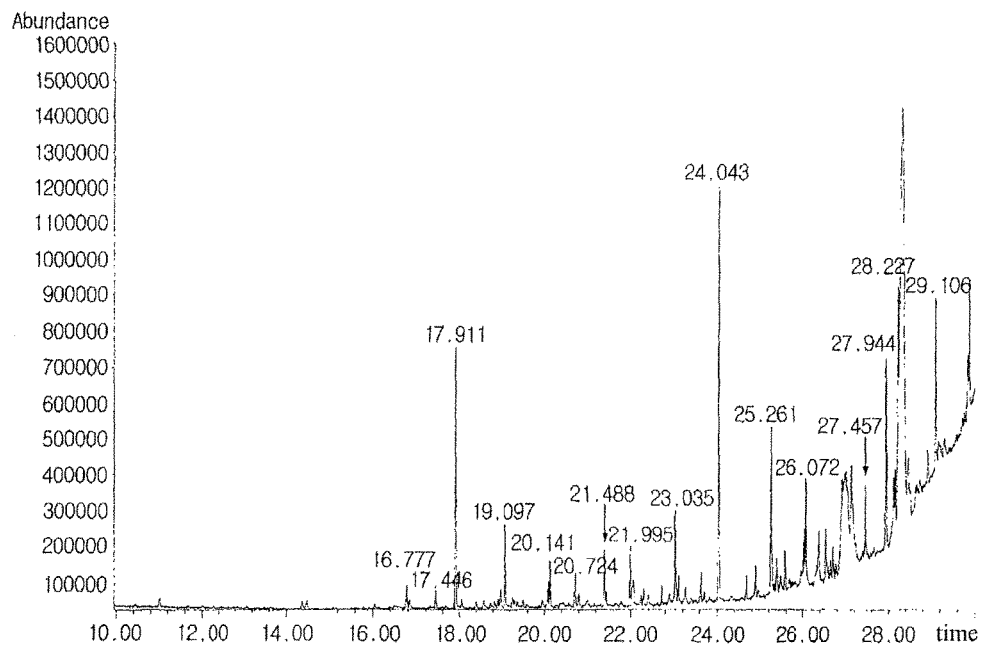

[Figure 6]
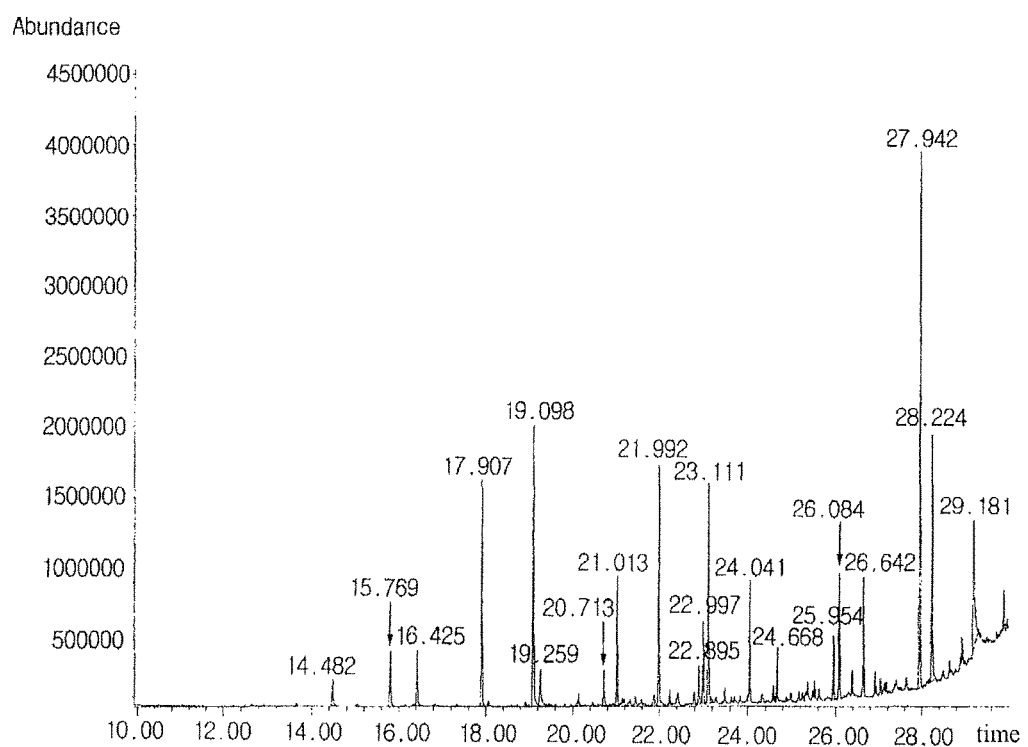

PREPARATION METHOD OF TEA WATER, AND TEA WATER OBTAINED THEREBY

CROSS-REFERENCE TO RELATED APPLICATIONS

This application is a divisional of U.S. patent application Ser. No. 13/512,538, filed on May 29, 2012, the disclosure of which is incorporated in its entirety by reference herein, and which is the national stage of international application no. PCT/KR2010/008517, filed on Nov. 30, 2010, which claims priority to Korean patent application no. 10-2009-0116703, filed on Nov. 30, 2009, the entirety of which is incorporated by reference herein.

TECHNICAL FIELD

The present disclosure relates to a method for preparing tea water and tea water obtained thereby.

BACKGROUND ART

Tea for drinking is one obtained by deactivating oxygenase present in shoots or leaves of theaceous *Camellia sinensis* and removing water therefrom. Tea has been enjoyed as favorite food from old times before the birth of Christ. In addition, it has been shown that active ingredients, such as catechins, amino acids, vitamin C, beta-carotene and dietary fibers, contained in tea have valuable pharmacological mechanisms. Particularly, various effects, including an anti-oxidative effect, anti-aging effect, anti-cancer effect, effect of reducing cholesterol in blood, effect of detoxifying heavy metals, effect of preventing a tooth decay and an effect of removing bad breath, provided by the ingredients contained in tea have been demonstrated, and thus tea has received great attention.

DISCLOSURE

Technical Problems

The present disclosure is directed to providing a method for preparing tea water causing little skin irritation in an eco-friendly, cost-efficient and energy-efficient manner, the method including deactivating enzymes of raw tea leaves and extracting juice therefrom to obtain tea juice, and removing ions from the tea juice to obtain tea water.

The present disclosure is also directed to providing tea water obtained by removing ions from tea juice of raw tea leaves in which enzymes are deactivated, the tea water having a reduced amount of such ingredients as hexanol, z-3-hexenol or linalool to reduce skin irritation.

Technical Solution

In one general aspect, there is provided a method for preparing tea water, including deactivating enzymes of raw tea leaves and extracting juice therefrom to obtain tea juice, and removing ions from the tea juice to obtain tea water.

In another general aspect, there is provided tea water obtained by removing ions from tea juice of raw tea leaves in which enzymes are deactivated.

In still another general aspect, there are provided a cosmetic composition, food composition and a pharmaceutical composition including the tea water.

Advantageous Effects

Since the method for preparing tea water disclosed herein uses raw tea leaves, energy consumption is low and byproducts to be discarded are minimized, thereby reducing production cost and contributing to environmental protection. In addition, the method requires no processing of tea leaves, and thus provides tea water in a more rapid and efficient manner.

Further, the tea water disclosed herein has a low amount of skin irritating ingredients, and thus causes little skin irritation. Therefore, a cosmetic composition and pharmaceutical composition including the tea water cause little skin irritation.

DESCRIPTION OF DRAWINGS

FIG. 1 is a schematic view illustrating a method for preparing tea water.

FIG. 2 is a graph showing the results of quantitative analysis of Example 1 using gas chromatography.

FIG. 3 is a graph showing the results of quantitative analysis of Example 2 using gas chromatography.

FIG. 4 is a graph showing the results of qualitative analysis of Comparative Example 2 using gas chromatography.

FIG. 5 is a graph showing the results of qualitative analysis of Comparative Example 3 using gas chromatography.

FIG. 6 is a graph showing the results of qualitative analysis of Example 1 using gas chromatography.

BEST MODE

Raw tea leaves include 80-85% of water, 10-15% of fibrin, 2-5% of polyphenol and 1-5% of other ingredients. In general, in the case of water to be combined with a cosmetic composition, ion-purified water having a few types of or a low amount of ions dissolved in water is used. This is because a large amount of ions contained in water may interrupt effects of a cosmetic composition containing a surfactant, emulsifier or the like, and may affect stability of the cosmetic composition. Particularly, such a large amount of ions reduce the viscosity of a viscous composition with time. In general, liquid obtained by infusing processed tea leaves contains $F^-$, $Cl^-$, $NO_3^-$, $PO_4^-$ and $SO_4^-$ at a concentration of 100-3000, 500-2500, 0-200, 200-5000 and 50-3000 μg per 100 g of water, respectively. Therefore, considering such ions contained in liquid obtained by infusing processed tea leaves, it is required to infuse tea leaves in water within the possible shortest time (regardless of concentration desired for drinking) so that a very low concentration is obtained. However, in this case, the liquid obtained by infusing tea leaves may not contain valuable ingredients contained originally in tea leaves.

Unlike methods for preparing tea water according to the related art, the method for preparing tea water disclosed herein includes deactivating enzymes of raw tea leaves, extracting juice therefrom and removing such ions. Thus, it is possible to obtain tea water still including water and valuable ingredients contained in raw tea leaves.

Processing of tea leaves, as expressed most simply, means removing water contained in tea leaves at a constant rate. In such processing of tea leaves, a considerable amount of energy is required to remove water contained in tea leaves. Since tea water according to the related art uses processed tea, additional energy and processes are required to infuse tea leaves, which already have consumed a great amount of energy during thermal processing. This requires high production cost and causes excessive energy consumption, and thus is not favorable in terms of environmental protection. In addition, solids remaining after infusing the processed tea leaves should be discarded, resulting in formation of additional discharge.

On the contrary, the method disclosed herein uses raw, non-processed tea leaves, and thus energy consumption caused by heat treatment is low to minimize energy consumption. Further, the method disclosed herein may contribute to environmental protection. In addition, tea solids remaining after preparing tea water according to the present disclosure may be introduced to a process for producing general tea drink products, or may be suitable as raw materials for green tea when an additional drying process is used. Therefore, it can be said that the method disclosed herein, which reduces energy consumption and minimizes byproducts to be discarded, is an eco-friendly method.

In addition, unlike methods for preparing tea water from tea leaves by using additional dissolution water according to the related art, the method for preparing tea water disclosed herein is characterized by including deactivating enzymes of raw tea leaves, extracting juice therefrom, removing ions to obtain tea water, and aging the tea water.

As used herein, the term 'tea water' means all types of liquids derived from tea leaves, in a broad sense. Particularly, tea water includes water obtained after infusing non-processed or processed tea leaves, tea leave extract, liquid obtained by condensing vapor generated by heating tea leaves, liquid obtained by steaming tea leaves, adding cold water or ion water thereto and performing extraction, or the like. The tea water contains ingredients helpful to humans as well as water contained in tea leaves.

Hereinafter, the method will be described in more detail.

In one aspect, there is provided a method for preparing tea water, comprising:

deactivating enzymes of raw tea leaves and extracting juice therefrom to obtain tea juice; and removing ions from the tea juice to obtain tea water.

According to an embodiment, the method further comprises aging the tea water, after the tea water is obtained.

According to another embodiment, the term 'tea leaves' means shoots or leaves of *Camellia sinensis* regardless of the quality or type thereof. Particularly, tea harvested in all seasons of spring, summer and autumn, and gyokuro tea having an increased amount of chlorophyll by using a sunscreen may be used, but the tea leaves that may be used herein are not limited thereto. According to a particular embodiment, the term 'raw tea leaves' refers to non-processed tea leaves.

According to still another embodiment, raw tea leaves may be subjected to pretreatment before the tea juice is obtained. Such pretreatment generally includes collecting leaves from a tea tree, washing the leaves with purified water to remove foreign materials, and removing water droplets attached to the surfaces of tea leaves by using a dewatering system. The tea leaves may be stored at a low temperature (4-10° C.) to compensate for heat generated from the tea leaves.

According to an embodiment, to obtain the tea juice in the method, raw tea leaves are subjected to steaming, heating or pressurization to deactivate enzymes of the raw tea leaves. According to another embodiment, to obtain the tea juice in the method, raw tea leaves are subjected to steaming to deactivate enzymes of the raw tea leaves. When steaming the raw tea leaves, steaming may be carried out at a temperature of 100-150° C., particularly 102-121° C., and more particularly 105-112° C. Enzymes of raw tea leaves are deactivated by such steaming treatment. In addition, such steaming treatment makes plant cell tissues soft, thereby increasing yield of tea juice.

According to an embodiment, when the raw tea leaves in which enzymes are deactivated are subjected to juice extraction to obtain tea juice, the juice extraction may be carried out by at least one method selected from the group consisting of gear-based juice extraction, press-based juice extraction, crushing-based juice extraction and enzymatic decomposition-based juice extraction.

According to another embodiment, after the tea juice is obtained, it may be further passed through a net. By doing so, solids remaining in the tea juice are removed. According to an embodiment, the net may have a size of 10-400 mesh. According to another embodiment, the net may have a size of 30-200 mesh. According to still another embodiment, the net may have a size of 80-120 mesh.

According to an embodiment, when the tea water is obtained, ions are removed from the tea juice by a vaporization and liquefaction process or an osmotic filtering process. By doing so, it is possible to remove ions, which may interrupt desired effects of a cosmetic composition or may affect stability the composition, from the tea juice. Hereinafter, the vaporization and liquefaction process will be explained in more detail. The tea juice is heated to perform vaporization, wherein heating may be performed at a temperature of about 100-121° C. under pressure. In a variant, heating may be carried out at a temperature of about 80-100° C. under ambient pressure. In another variant, heating may be carried out at a temperature of about 40-80° C. under reduced pressure.

According to an embodiment, after ions are removed from the tea juice to obtain tea water, the tea water may be further subjected to centrifugal separation, membrane separation or distillation separation to remove and separate undesired ingredients. According to another embodiment, the tea water, from which undesired ingredients are removed and separated, may be mixed with a predetermined amount of organic solvent and then the solvent may be removed selectively via distillation, so that ingredients having low preference or undesired ingredients may be separated and removed selectively. According to an embodiment, the organic solvent may be ethyl alcohol. Ethyl alcohol may be used in an amount of 5-40 wt % based on the total weight of tea water.

According to an embodiment, after the tea water is obtained, it may be further subjected to aging. Through such aging, it is possible to remove skin irritating ingredients, such as hexanol, z-3-hexenol or linalool. When aging the tea water, aging may be performed at 0-120° C. for 12-24 hours. According to another embodiment, aging may be performed at 80-120° C. for 12-24 hours under pressure in such a condition that water is not evaporated from the tea water. According to still another embodiment, aging may be performed under ambient pressure at 40-80° C. for 12-24 hours. According to yet another embodiment, aging may be performed under reduced pressure at 4-40° C. for 12-24 hours.

In the method for preparing tea water according to an embodiment, the 5 resultant tea water may satisfy at least one of the following conditions: a concentration of linalool of 5 μg/mL or less, a concentration of hexanol of 0.2 μg/mL or less, and a concentration of z-3-hexenol of 0.2 μg/mL or less. In the method for preparing tea water according to another embodiment, the resultant tea water may satisfy at least one of the following conditions: a concentration of linalool of 1 μg/mL 10 or less, a concentration of hexanol of 0.1 μg/mL or less, and a concentration of z-3-hexenol of 0.1

μg/mL or less. In the method for preparing tea water according to still another embodiment, the resultant tea water may satisfy at least one of the following conditions: a concentration of linalool of 0.5 μg/mL or less, a concentration of hexanol of 0.02 μg/mL or less, and a concentration of z-3-hexenol of 0.02 μg/mL 15 or less. As such, the tea water disclosed herein contains a very low amount of skin irritating ingredients, including hexanol, z-3-hexenol or linalool, and thus causes little skin irritation.

In another aspect, there is provided tea water obtained by removing ions from tea juice of raw tea leaves in which enzymes are deactivated.

According to an embodiment, the tea water may satisfy at least one of the following conditions: a concentration of linalool of 5 μg/mL or less, a concentration of hexanol of 0.2 μg/mL or less, and a concentration of z-3-hexenol of 0.2 μg/mL or less. According to another embodiment, the tea water may satisfy at least one of the following conditions: a concentration of linalool of 1 μg/mL or less, a 25 concentration of hexanol of 0.1 μg/mL or less, and a concentration of z-3-hexenol of 0.1 μg/mL or less. According to still another embodiment, the tea water may satisfy at least one of the following conditions: a concentration of linalool of 0.5 μg/mL or less, a concentration of hexanol of 0.02 (μg/mL or less, and a concentration of z-3-hexenol of 0.02 μg/mL or less. As such, the tea water disclosed herein contains a significantly reduced amount of skin irritating ingredients. In addition, the tea water meets the standards applicable to a cosmetic composition.

In still another aspect, there is provided a cosmetic composition including tea water obtained by removing ions from tea juice of raw tea leaves in which enzymes are deactivated. Particularly, the tea water disclosed herein may be used as a base for a cosmetic composition.

The cosmetic composition includes a cosmetically or dermatologically acceptable medium or base. The cosmetic composition includes any forms suitable for topical application, and particular examples thereof include solution, gel, solid, anhydrous slurry products, oil in water emulsion, water in oil emulsion, multiemulsion, suspension, microemulsion, microcapsules, microgranules or ionic (liposome) and non-ionic follicular dispersion, or cream, skin, lotion, powder, ointment, spray, cleanser or conceal stick. The composition disclosed herein may be used in the form of foam or an aerosol composition further including a pressurized propellant. Such compositions may be obtained by a conventional method.

The cosmetic composition may further include other adjuvants that may not adversely affect a main desired effect or may provide a synergic effect to the main effect. In addition to the active ingredients, other ingredients may be selected and added with ease by those skilled in the art depending on the particular form or purpose of a cosmetic composition.

For example, the cosmetic composition may further include a skin absorption-enhancing material to improve its effect. In addition, the cosmetic composition disclosed herein may include a material selected from the group consisting of water soluble vitamins, oil-soluble vitamins, polymer peptides, polysaccharides, spingolipids and seaweed extract. Further, the cosmetic composition disclosed herein may include other ingredients currently used in the field of cosmetics in addition to the active ingredients, and particular examples thereof include oil and fat ingredients, moisturizing agents, emollients, surfactants, organic and inorganic pigments, organic powder, UV absorbing agents, preservatives, disinfecting agents, antioxidants, plant extract, pH modifiers, alcohols, dyes, aromatic, blood circulation stimulating agents, cooling agents, antiperspirants, purified water, or the like. Ingredients that may be added to the cosmetic composition disclosed herein are not limited to the above-listed materials, and are used in such a manner that they may not adversely affect the purpose and effect of the present disclosure.

There is no particular limitation in formulation of the cosmetic composition and any formulation may be selected as desired. For example, the cosmetic composition may be provided as one or more formulations selected from the group consisting of skin softeners (skin lotion and milk lotion), nourishing lotion, essence, nourishing cream, massage cream, powder, lipstick, makeup base, foundation, patches, spray, pack, gel, essence, eye cream, eye essence, cleansing cream, cleansing foam, cleansing water, cleanser, body lotion, body cream, body oil and body essence, but is not limited thereto.

The tea water may be used in an amount of 0.01-100 wt % based on the total weight of the cosmetic composition.

In still another aspect, there is provided a food composition including tea water obtained by removing ions from tea juice of raw tea leaves in which enzymes are deactivated. There is no particular limitation in the form of the food composition. The food composition may be provided as a solid or drink. The tea water may be used in an amount of 0.01-100 wt % based on the total weight of the food composition.

In yet another aspect, there is provided a pharmaceutical composition including tea water obtained by removing ions from tea juice of raw tea leaves in which enzymes are deactivated. Particularly, the tea water may be used as a base for a pharmaceutical composition.

When applying the composition disclosed herein to pharmaceuticals, a conventional inorganic or organic carrier is added to the composition, so that the composition may be formulated into a solid, semi-solid or liquid form for oral or parenteral administration. The composition may be formulated with ease by a currently used method. In addition, surfactants, vehicles, colorants, spices, stabilizers, preservatives, antibacterial agents, hydrating agent, emulsification accelerators, suspending agents, salts and/or buffers for controlling osmotic pressure, and other conventional adjuvants may be used in a suitable manner.

For oral administration, tablets, pills, granules, soft and hard capsules, dusts, fine particles, powder, liquid, emulsion, syrup, pellets or the like may be used. Such formulations may further include diluents (for example, lactose, dextrose, sucrose, mannitol, sorbitol, cellulose or glycine), lubricants (for example, silica, talc, stearic acid and magnesium or calcium salts thereof or polyethylene glycol), or a binder (for example, magnesium aluminum silicate, starch paste, gelatin, tragacanth, methyl cellulose, sodium carboxymethyl cellulose or polyvinyl pyrrolidine), in addition to the active ingredients. If necessary, such formulations may further include other pharmaceutical additives, for example, a disintegrating agent, such as starch, agar, alginic acid or a sodium salt thereof, adsorbing agent, coloring agent, flavor or sweetener. Tablets may be obtained by conventional mixing, granulation or coating 5 processes.

Meanwhile, formulations for parenteral administration include skin application formulations, or injection formulation, drops, lotion, ointment, gel, cream, suspension, emulsion, suppositories, patches or spray formulations, but are not limited thereto.

The pharmaceutical composition disclosed herein may be administered via oral, parenteral, rectal, local, transdermal, intravenous, intramuscular, intraperitoneal, subcutaneous routes, or the like.

In addition, the dose of active ingredients may be varied with the age, sex and body weight of a subject to be treated, particular disease or pathological condition to be treated, severity of disease or pathological condition, administration route and the judgment of a prescriber. Determination of the effective dose may be made by those skilled in the art based on the above-mentioned factors.

The tea water may be used in an amount of 0.01-100 wt % based on the total weight of the pharmaceutical composition.

Mode for Disclosure

The examples, comparative examples and test examples will now be described. The following examples, comparative examples and test examples are for illustrative purposes only and not intended to limit the scope of this disclosure.

Example 1

First, 2 kg of raw tea leaves within several hours after harvest are allowed to be in contact with steam generated at 100° C. for 2-3 minutes to deactivate enzymes, and then introduced to two screw gear type juicers to separate tea juice from solids. The tea juice is passed through an 80-mesh net to remove the remaining solids. The tea juice is introduced to a depressurized concentration system and subjected 5 to distillation at 40-80° C., and thus the generated vapor is condensed to obtain tea water. The resultant tea water is packed under sterilization with a 0.2 μm sterilization filter in an aseptic clean bench to provide Example 1.

Example 2

The tea water obtained from Example 1 is introduced to a depressurized concentration system and aged for 24 hours under the conditions of 28° C., 40 mmHg and 10 rpm. The aged tea water is packed under sterilization with a 0.2 μm sterilization filter in an aseptic clean bench to provide Example 2.

Example 3

First, 2 kg of raw tea leaves within several hours after harvest are allowed to be in contact with steam generated at 100° C. for 2-3 minutes to deactivate enzymes, and then introduced to two screw gear type juicers to separate tea juice from solids. The tea juice is passed through an 80-mesh net to remove the remaining solids. The tea juice is introduced to a depressurized concentration system and subjected to distillation at 40-80° C., and thus the generated vapor is condensed to obtain tea water. To the resultant tea water, 97% alcohol is added in an amount of 5 wt % based on the total weight of the tea water, followed by mixing for 3 minutes. Then, ethyl alcohol is separated via distillation using a depressurized distillation system at 30-50° C. The tea water from which alcohol is removed is packed under sterilization with a 0.2 μM sterilization filter in an aseptic clean bench to provide Example 3.

Comparative Example 1

First, 20 g of raw tea leaves within several hours after harvest are dipped in a mortar containing liquid nitrogen to freeze instantaneously, and ground finely to crush cells totally. Then, the treated tea leaves are passed through a 200-mesh net, and extracted by using a screw gear type juicer to provide Comparative 5 Example 1.

Comparative Examples 2 and 3

Tea leaves harvested at a time similar to the harvest time of the raw tea leaves used in Example 1 are treated preliminarily through steaming—rubbing and drying (j° u)—rubbing (yunyum)—rubbing under hot air (jeungyu)—trimming and 10 drying (jungyu)—drying processes. Then, 20 g of the preliminarily treated tea leaves are dipped into purified water at 70° C. for 2 minutes and filtered through a 200-mesh net to provide Comparative Example 2. The preliminarily treated tea leaves are further treated through heating—sieving—cutting—stem selection—mixing processes, and then 20 g of the further treated tea leaves are dipped into purified water at 70° C. for 2 minutes and filtered through a 200-mesh net to provide Comparative Example 3.

[Test Example 1] Evaluation of Yield

First, 2 kg of raw tea leaves are not steamed but directly subjected to juice extraction using a juicer, followed by centrifugal separation, to obtain a supernatant as a product. In addition, the tea juice, obtained by extracting juice from the tea leaves subjected to steaming according to Example 1, is subjected to centrifugal separation to obtain a supernatant as a product. The two supernatant products and the product obtained by extracting juice according to Comparative Example 1 are evaluated for yields on the basis of tea leaves. The results are shown in the following Table 1. Each yield is calculated according to the following Mathematical Formula 1.

Yield=(Liquid obtained by extracting juice/Raw tea leaves)×100     [Mathematical Formula 1]

TABLE 1

|  | Raw tea leaves | Steamed tea leaves | Tea leaves obtained by nitrogen freezing and crushing |
|---|---|---|---|
| Yield | 25% | 35% | 11% |

The steamed tea leaves provide the highest yield, while the tea leaves obtained by nitrogen freezing and crushing provide the lowest yield. It is thought that such results are derived from the fact that extracting juice after softening plant tissues by steaming enables separation of a larger amount of water.

[Test Example 2] Evaluation of Ingredients

Examples 1 and 2 and Comparative Examples 2 and 3 are subjected to gas chromatography analysis by solid phase microextraction (SPME). After carrying out quantitative analysis, the gas chromatograms of Examples 1 and 2 are shown in FIG. 2 and FIG. 3, respectively. Particularly, the results of Example 1 are also 15 shown in the following Table 2.

TABLE 2

| No. | Retention Time (min) | Compound |
|---|---|---|
| 1 | 2.958 | Hexanol |
| 2 | 3.09 | 2-propanone |

TABLE 2-continued

| No. | Retention Time (min) | Compound |
|---|---|---|
| 3 | 3.749 | 3-butane |
| 4 | 3.957 | 2-ethoxy-2-methylpropane |
| 5 | 4.359 | 3-methylbutanal |
| 6 | 4.486 | 2-methylbutanal |
| 7 | 4.735 | 1-penten-3-ol |
| 8 | 4.835 | Tetrahydro-2,2,5,5-tetramethylfuran |
| 9 | 5.514 | 3-butyronitrile |
| 10 | 6.192 | 1-pentanol |
| 11 | 7.879-8.119 | z-3-hexenol |
| 12 | 9.273 | 4-hydroxy-4-methyl-2-pentanone |
| 13 | 9.412 | 4-methyl-2-heptanone |
| 14 | 12.085 | Linalool |

Among the main ingredients of tea, those having a low sensory threshold and thus allowing humans to distinguish them immediately include the following three ingredients: hexanol, z-3-hexenol and linalool. Particularly, it is known that 5 linalool causes allergy upon direct contact with skin. As can be seen from the above results, Example 2 includes a lower amount of linalool as compared to Example 1.

The following Table 3 shows the results of gas chromatography analysis of Examples 1 and 2 mainly about the three ingredients having a low sensory 10 threshold.

TABLE 3

| Compound | Retention Time (min) | Peak area Example 1 | Peak area Example 2 | Peak area Example 3 | Concentration (µg/mL) Example 1 | Concentration (µg/mL) Example 2 | Concentration (µg/mL) Example 3 |
|---|---|---|---|---|---|---|---|
| Hexanol | 2.958 | 6.22 | 2.31 | 4.11 | 0.04 | 0.01 | 0.02 |
| z-3-hexenol | 7.879-8.119 | 44.14 | 3.67 | 40.52 | 0.14 | 0.01 | 0.13 |
| Linalool | 12.085 | 156.02 | 60.51 | 140.18 | 1.21 | 0.48 | 1.05 |

The concentration of each of the three ingredients is significantly reduced in Example 2 as compared to Example 1. Particularly, the concentration of linalool, which causes skin allergy, is reduced by about 56%. Therefore, it can be seen that aged tea water shows a lower degree of skin allergy as compared to non-aged tea water. In the case of Example 3, hexanol with a low molecular weight is reduced slightly by treatment with ethyl alcohol but the other two ingredients are not reduced 5 significantly due to the lack of aging time.

Meanwhile, the gas chromatograms obtained after the qualitative analysis of Comparative Examples 2 and 3 are shown in FIG. 4 and FIG. 5, respectively. In addition, the gas chromatograms obtained after qualitatively analyzing Comparative Examples 2 and 3 in comparison with Example 1 are shown in FIG. 6. The 10 ingredients corresponding to the peaks of FIG. 6 are shown in the following Table 4. Referring to FIG. 4 and FIG. 5, some peaks that are not present in FIG. 6 appear. It is thought that the peaks are derived from pyrazine-like aromatic ingredients having a good taste and modified from the unique ingredients of raw tea leaves. Such ingredients may cause skin irritation, and thus are not suitable for a 15 cosmetic composition and pharmaceutical composition.

TABLE 4

| Retention Time (min) | Compound |
|---|---|
| 14.482 | z-3-hexen-1-ol |
| 15.769 | Trans-linalool |
| 16.425 | Linalool oxide A |

TABLE 4-continued

| Retention Time (min) | Compound |
|---|---|
| 17.907 | 1,6-octadiene-3-ol |
| 19.098 | Carbitol |
| 20.713 | Linalool oxide D |
| 21.013 | 2H-pyran-3-ol |
| 21.992 | Linalool |
| 22.895 | 1,4-butanediol |
| 22.997 | Benzylnitrile |
| 23.111 | Jasmone |
| 24.668 | Butylated hydroxytoluene |
| 25.954 | Muloool |
| 27.942 | Indole |
| 28.224 | Benzophenone |

[Test Example 3] Basis Analysis

Basic analysis of Example 1 is carried out to determine pH, refractive index, specific gravity, heavy metal content, count of bacteria or fungi, or the like. The 5 results are shown in the following Table 5.

TABLE 5

| | Example 1 | Example 2 | Example 3 |
|---|---|---|---|
| pH | 5.82 | 5.98 | 5.75 |
| Refractive index | 1.333 | 1.341 | 1.320 |
| Specific gravity | 1.002 | 0.993 | 1.001 |
| Pb | 0.0760 mg/kg | 0.0770 mg/kg | 0.0761 mg/kg |
| As | 0.0674 mg/kg | 0.0676 mg/kg | 0.0670 mg/kg |
| Bacterial count | 12/mL | 10/mL | 5/mL |
| Fungal count | Not detected | Not detected | Not detected |

As can be seen from the foregoing, Examples 1 to 3 satisfy the standards applicable to a cosmetic composition.

[Test Example 4] Test for Safety Against Skin Irritation

Forty male and female adult subjects (39 women and 1 man) having an average age of 41.3 (21-59) are tested for skin irritation after using Example 1 and Example 2. Herein, subjects suffering from psoriasis, acne, eczema or other skin diseases, pregnant or lactating women, or subjects taking an antihistamine agent or the like are excluded from the test.

A covering patch to which a dressing containing a test substance at a concentration of 100% is applied at a dose of 20 µL/chamber (IQ chamber) is 5 attached to the back portion of each subject for 24 hours, and the test portion is observed up to 48 hours. A degree of expression of skin irritation is evaluated as a score, wherein a score less than 1 is taken as grade I (no skin irritation), a score less than 3 is taken as grade II (light skin irritation), a score less than 5 is taken as grade III (moderate skin irritation), and a score of 5 or higher is taken as grade IV (severe skin irritation). Each grade is based on a modification of the test standards defined by CTFA GUIDELINE (1981) and Frosch & Kligman (1979), and the criteria are shown in the following Table 6. The test results are shown in the following Table 7.

TABLE 6

| Patch test criteria about inflammation degrees | |
|---|---|
| Grade | Characteristics |
| 0 | No reaction |
| I | Slight erythema, spots or rash |
| II | Moderate uniform erythema |
| III | Strong erythema with edema |
| IV | Strong erythema with edema and blister |

TABLE 7

| Test substance | 24 hr | | | | 48 hr | | | | Average score | Evaluation (grade) |
|---|---|---|---|---|---|---|---|---|---|---|
| | +1 | +2 | +3 | +4 | +1 | +2 | +3 | +4 | | |
| Example 1 100% | 6 | — | — | — | 2 | — | — | — | 2.50 | II |
| Example 2 100% | — | — | — | — | — | — | — | — | 0.00 | I |

As can be seen from Table 7, Example 2 shows lower skin irritation as compared to Example 1. In other words, aged tea water causes lower skin irritation as compared to non-aged tea water. It is though that such results are derived from the fact that aged tea water has a lower amount of skin irritating ingredients, such as hexanol, z-3-hexenol and linalool.

The invention claimed is:

1. A method for preparing aged tea water, comprising:
   deactivating enzymes of raw tea leaves by subjecting the raw tea leaves to steaming, and extracting juice therefrom to obtain tea juice, wherein the raw tea leaves are non-processed tea leaves;
   removing ions from the tea juice to obtain tea water; and
   aging the tea water at 0-120° C. for 12-24 hours,
   wherein the aged tea water comprises; linalool in an amount of 5 μg/mL or less; hexanol in an amount of 0.2 μg/mL or less; and/or z-3-hexenol an amount of 0.2 μg/mL or less.

2. The method according to claim 1, wherein the ions are removed from the tea juice by subjecting the tea juice to a vaporization and liquefaction process, or an osmotic filtering process to provide the tea water.

3. The method according to claim 1, wherein the step of aging the tea water occurs at 40-80° C. for 12-24 hours.

4. The method according to claim 1, wherein the step of aging the tea water occurs at 4-40° C. for 12-24 hours.

5. The method according to claim 1, wherein the step of aging the tea water occurs under pressure.

* * * * *